United States Patent [19]

Garland et al.

[11] Patent Number: 5,304,465
[45] Date of Patent: Apr. 19, 1994

[54] ENZYME ASSAY METHOD USING SURFACE PLASMON RESONANCE SPECTROSCOPY

[75] Inventors: Peter B. Garland, Old Bosham; Philip G. Malan, Hearne, both of England

[73] Assignee: Amersham International plc, Buckinghamshire, United Kingdom

[21] Appl. No.: 768,211
[22] PCT Filed: Jun. 11, 1990
[86] PCT No.: PCT/GB90/00898
§ 371 Date: Oct. 11, 1991
§ 102(e) Date: Oct. 11, 1991
[87] PCT Pub. No.: WO90/15983
PCT Pub. Date: Dec. 27, 1990

[30] Foreign Application Priority Data

Jun. 12, 1989 [GB] United Kingdom ............... 8913474

[51] Int. Cl.$^5$ .................... C12Q 1/00; G01N 1/22; G01N 21/55; G01J 3/30
[52] U.S. Cl. .................... 435/4; 435/7.91; 435/7.95; 422/82.05; 422/85; 422/68.1; 422/91; 356/318; 356/445
[58] Field of Search .............. 422/82.05, 85, 91, 68.1; 356/318, 445; 435/4, 7.91, 7.95

[56] References Cited

U.S. PATENT DOCUMENTS 4,877,747 10/1989 Stewart .................. 436/525
5,064,619 11/1991 Finlan .................. 422/82.05

FOREIGN PATENT DOCUMENTS 2202045A 9/1988 United Kingdom .

OTHER PUBLICATIONS

Sigma Chemical Co Catalog 1992 St. Louis, Mo. p. 254.

Primary Examiner—Michael G. Wityshyn
Assistant Examiner—Ralph G. Itomer
Attorney, Agent, or Firm—Wenderoth, Lind & Ponack

[57] ABSTRACT

Method of performing enzyme assays using the technique of surface plasmon resonance spectrometry (SPRS). An SPRS surface carries an immobilized reagent which is capable of being released by an enzyme. A fluid sample containing the enzyme is brought into contact with the solid surface, and release of the reagent monitored by SPRS.

5 Claims, No Drawings

ENZYME ASSAY METHOD USING SURFACE PLASMON RESONANCE SPECTROSCOPY

This invention concerns methods of performing enzyme assays using the technique of surface plasmon resonance spectrometry (SPSR).

The phenomenon of SPR is well known and will not be described in detail (see EPA 305109 for example). Briefly, the intensity of monochromatic plane-polarised light (conveniently obtained from a laser) reflected from the interface between an optically transparent material, e.g. glass, and metal depends on the refractive index of material on the downstream side of the metal. Accordingly, by measuring changes in intensity of reflected light an indication can be obtained of changes in refractive index of material at a particular point on the downstream surface of the metal. The intensity of reflected light also varies with the angle of incidence, and reflectively drops sharply to a minimum at a particular angle which is characteristic of the equipment.

International Patent Application PCT/GB90/00432 filed Mar. 21, 1990 makes use of this phenomenon in an enzyme assay. The solid surface carries thereon an immobilized enzyme which catalyses the reaction between two or more reactants resulting in the production of a reaction product, or a substrate for the enzyme. The method involves bringing into contact with the solid surface a fluid medium containing the remaining reactants and if not already present the enzyme, under conditions to cause the reaction product to be deposited on the solid surface. One molecule of enzyme can catalyze the deposition of many molecules of reaction product on the solid surface. The change in refractive index that results from deposition of the reaction product is monitored by SPRS. That method provides a satisfactory assay for the enzyme, but one which requires the addition of one or more reagents to the fluid medium.

This invention is a development of that method, and has the advantage that no additional reagents are required, apart from a pretreated solid surface and a liquid sample of the analyte.

a method of performing an assay for an enzyme according to the invention involves the use of a solid surface carrying an immobilized reagent which is capable of being released by the enzyme. A fluid sample is brought into contact with the immobilised reagent under conditions such that the enzyme if present in the sample catalyzes release of the reagent from the surface. The solid surface is provided by a metallic layer applied to a block of material transparent to electromagnetic radiation. Release of the reagent from the surface of the metallic layer is assayed by SPRS.

The immobilized reagent may be a substrate for the enzyme. Examples of suitable pairs of enzyme and substrate are DNAse/DNA; RNAse/RNA; amylase/starch; various glycosidases/their polysaccharide substrates; peptidases/polypeptides. In addition to these natural substrates, synthetic substrates can be made combining a molecule or particle (of high or alternatively low refractive index with respect to the bulk phase) with the metal surface via an enzymatically sensitive linker that is cleavable by the enzyme under study. Release of the molecule or particle is then easily detected as a change in the SPRS signal.

As noted above, a major advantage of this technique is that it requires no reagent other than the enzyme substrate pre-coated on the solid surface of the SPR device. A further advantage is its directness. The technique also meets a need—the classes and types of enzymes suited for this approach are very difficult to assay directly and at high sensitivity by any other means.

It is not necessary that the enzyme be the primary analyte under study. There are very many assays in existence for a variety of analytes which result in the production of an enzyme in solution at a concentration related to the concentration of primary analyte in a sample. This invention provides a convenient and rapid technique for observing the presence of concentration in a fluid of an enzyme from any source.

EXAMPLE

A glass slide coated with 50 nm thick silver-metal was placed on a fan beam SPR instrument. The silver surface was coated by flowing about 0.5 ml of 200 nM mouse anti-sheep immunoglobulin (MaS) made up in 10 mM phosphate buffer, pH 7.4, over the surface at a rate of 4 $\mu$l/sec. The surface was then washed by manual application of 3 ml of 10 mM phosphate buffer, followed by the same volume of 10 mM borate buffer, pH 8.5.

Various concentrations of Pronase E (Protease XXV, from Streptomyces griseus, 4.7 units/mg, Sigma Chemical Co.) as specified below were prepared freshly in borate buffer, pH 8.5, immediately before use, by dilution from a stock of 1.4 mg/ml (equivalent to about 52 $\mu$M enzyme, made by dissolving 4.4 mg Pronase E in 3.1 ml borate buffer) that had been prepared at the beginning of the day. The enzyme solution (about 0.5 ml) volume was pumped over the surface at a flow-rate of 4 $\mu$l/sec. The base-line change after reaction was measured by performing a manual wash with borate buffer.

The buffer was then changed back to 10 mM phosphate, pH 7.4. The residual enzyme activity at the surface, and any exposed binding sites at the surface were blocked by applying 3 ml of 0.5% bovine serum albumin plus 2 $\mu$M human gamma-globulin (both from Sigma) made up in 10 mM Phosphate, pH 7.4. The surface was washed with phosphate buffer, then 0.5 ml of 1.5 $\mu$M ovine IgG (oIgG) was pumped onto the surface. Any active antibody remaining on the surface would be expected to bind this protein. The surface was finally washed twice with phosphate buffer to obtain the amount of protein specifically bound.

During these protein, buffer washes and blocking additions, the change in percent reflectivity was measured on the SPR instrument. This change is directly related to the change in refractive index at up to 100 nm above the silver surface (i.e. about ten layers of IgG molecules could influence the SPR signal). The enzyme activity was calculated as the initial rate of change in percent reflectivity per second. The amount of mouse anti-sheep immuno-globulin bound at the surface was monitored by measuring the difference in percent reflectivity (%R) after and before protein addition ($\Delta$ % $R_{MaS}$). Similarly, the amount of ovine IgG bound was the difference between percent reflectivity after and before protein addition ($\Delta$ % $R_{oIgG}$). The results of the ovine IgG bound to the mouse anti-sheep immunoglobulin, to account for the difference between silver slides, was normalized by taking the ratio of $\Delta$ % $R_{oIgG}/\Delta$ % $R_{MaS}$. The fraction of mouse anti-sheep immunoglobulin removed was calculated as (1−(change in % reflectivity sheep-IgG)/(change in % reflectivity MaS).

| Results | | | |
|---|---|---|---|
| Enzyme Concentration (nM) | 80 | 200 | 220 |
| Rate of Hydrolysis (−Δ % R/sec) | 0.0038 | 0.0073 | 0.0098 |
| Fraction of MaS Removed (1 − Δ % $R_{oIgG}$/Δ % $R_{MaS}$) | 0.31 | 0.66 | 0.77 |

1. Protease hydrolysis of protein bound at the SPR surface.

A graph of these data gives a straight line passing through the origin, as would be expected for an enzyme rate is dependent on concentration.

2. Protease hydrolysis rate against the fraction of protein removed.

The enzymic reaction rate correlates with the fraction of antibody removed from the surface, as determined by back-titration of active antibody by measuring the binding of added ovine IgG. A straight line correlation that passes through the origin is expected.

We claim:

1. A method of performing an assay for an enzyme comprising:

providing a solid surface carrying an immobilized reagent which is capable of being released by the enzyme;

contacting the immobilized reagent with a fluid sample under conditions such that the enzyme, if present in the fluid sample, catalyzes release of the immobilized reagent from the solid surface; and detecting release of the immobilized reagent from the solid surface by surface plasmon resonance spectroscopy thereby determining the presence of the enzyme, wherein the solid surface is a metallic layer applied to a block of material transparent to electromagnetic radiation.

2. The method as claimed in claim 1, wherein the reagent is a substrate for the enzyme.

3. The method as claimed in claim 1, wherein the reagent comprises a molecule or particle, of high or low refractive index with respect to the fluid sample, joined to the surface by means of a bond which is cleavable by the enzyme.

4. The method as claimed in claim 1, wherein the reagent comprises a substrate for the enzyme, such that the enzyme and the substrate constitute an enzyme/substrate pair is selected from the group consisting of DNAse/DNA; RNAse/RNA; amylase/starch; glycosidases/polysaccharides; and peptidases/polypeptides.

5. The method as claimed in claim 4, wherein the enzyme is a peptidase and the reagent comprises a polypeptide.

* * * * *